(12) United States Patent
Neumann

(10) Patent No.: US 11,908,583 B2
(45) Date of Patent: Feb. 20, 2024

(54) APPARATUS AND METHOD FOR DETERMINING TOXIC LOAD QUANTIFIERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/734,449

(22) Filed: May 2, 2022

(65) Prior Publication Data
US 2023/0352179 A1    Nov. 2, 2023

(51) Int. Cl.
| | | |
|---|---|---|
| G16H 50/30 | (2018.01) | |
| G16H 20/60 | (2018.01) | |
| G16B 40/00 | (2019.01) | |
| G06N 20/00 | (2019.01) | |
| G06Q 30/0282 | (2023.01) | |

(52) U.S. Cl.
CPC ............ *G16H 50/30* (2018.01); *G06N 20/00* (2019.01); *G06Q 30/0282* (2013.01); *G16B 40/00* (2019.02); *G16H 20/60* (2018.01)

(58) Field of Classification Search
CPC ... G16H 10/00–80/00; G06Q 10/00–2250/905
See application file for complete search history.

(56) References Cited

U.S. PATENT DOCUMENTS

| | | | |
|---|---|---|---|
| 9,898,788 B1 | 3/2018 | Calargun et al. | |
| 10,121,036 B1 * | 11/2018 | Klein | G06K 7/1413 |
| 10,255,323 B1 * | 4/2019 | Guo | G06F 16/24561 |
| 10,902,351 B1 * | 1/2021 | Neumann | G16H 50/20 |
| 2006/0282411 A1 * | 12/2006 | Fagin | G06F 16/283 |

(Continued)

FOREIGN PATENT DOCUMENTS

| | | | | |
|---|---|---|---|---|
| CN | 113934863 A | * | 1/2022 | |
| EP | 2600269 A2 | * | 6/2013 | G06F 19/12 |

(Continued)

OTHER PUBLICATIONS

Mayr et al., "DeepTox: Toxicity Prediction using DeepLearning," FrontiersinEnvironmentalScience|www.frontiersin.org Feb. 2016 | vol. 3 | Article 8 (Year: 2016).*

(Continued)

*Primary Examiner* — Jonathon A. Szumny
(74) *Attorney, Agent, or Firm* — CALDWELL INTELLECTUAL PROPERTY LAW

(57) ABSTRACT

In an aspect an apparatus for determining toxic load quantifiers is presented. An apparatus includes at least a processor and a memory communicatively connected to the at least a processor. A memory contains instructions configuring at least a processor to receive user input comprising user data. At least a processor is configured to generate a query as a function of user data. At least a processor is configured to obtain query results as a function of a query. At least a processor is configured to determine a toxic load quantifier of a query results of query results as a function of a toxicity criterion and user data. At least a processor is configured to display a toxic load quantifier of query results to a user.

16 Claims, 7 Drawing Sheets

(56) References Cited

U.S. PATENT DOCUMENTS

| | | | | |
|---|---|---|---|---|
| 2010/0114917 | A1* | 5/2010 | Austin | G06Q 10/10 |
| | | | | 707/754 |
| 2016/0078182 | A1* | 3/2016 | Allen | G16H 50/20 |
| | | | | 702/19 |
| 2016/0224754 | A1* | 8/2016 | Hann | G16Z 99/00 |
| 2018/0226153 | A1* | 8/2018 | Rubenstein | G16H 50/50 |
| 2019/0008749 | A1* | 1/2019 | Harris | C10M 145/40 |
| 2019/0252036 | A1* | 8/2019 | Elemento | G16B 15/00 |
| 2019/0288837 | A1* | 9/2019 | St Amant | H04L 9/0894 |
| 2020/0175676 | A1* | 6/2020 | Tse | G06T 1/0007 |
| 2020/0227176 | A1* | 7/2020 | Eifert | G16H 20/10 |
| 2020/0364495 | A1* | 11/2020 | Stoettinger | G06F 18/2431 |
| 2021/0104300 | A1* | 4/2021 | Neumann | G16H 80/00 |
| 2021/0313029 | A1* | 10/2021 | Emmett | G16H 10/40 |
| 2022/0101972 | A1* | 3/2022 | Bajpai | G16H 70/40 |
| 2022/0152425 | A1* | 5/2022 | Da Silva Rodrigues | |
| | | | | A61N 5/1031 |
| 2022/0180991 | A1* | 6/2022 | Peters | G16H 20/10 |

FOREIGN PATENT DOCUMENTS

| | | | | |
|---|---|---|---|---|
| WO | WO-2008137450 | A2 * | 11/2008 | G06Q 30/00 |
| WO | WO-2022072346 | A1 * | 4/2022 | |

OTHER PUBLICATIONS

Nordlind et al., "In vitro effects of sodium lauryl sulfate on DNA synthesis and fine structure of human thymocytes," Int Arch Allergy Appl Immunol. 1986;81(2):165-9. i: 10.1159/000234126. (Year: 1986).*

Wu et al., "Machine Learning Based Toxicity Prediction: From Chemical Structural Description to Transcriptome Analysis," Int. J. Mol. Sci. 2018, 19, 2358; doi:10.3390/ijms19082358 (Year: 2018).*

Kim et al., "MRA Toolbox v. 1.0: a web-based toolbox for predicting mixture toxicity of chemical substances in chemical products," Scientific Reports | (2022) 12:8880 | (Year: 2022).*

US EPA, "User's Guide for T. E. S. T. (Toxicity Estimation Software Tool) Version 5.1—A Java Application to Estimate Toxicities and Physical Properties from Molecular Structure" Todd M. Martin U.S. Environmental Protection Agency Center for Computational Toxicology and Exposure (Year: 2020).*

Gualtieri et al., "WebFPTI: A tool to predict the toxicity/pathogenicity of mineral fibres including asbestos," Earth Science Informatics (2021) 14:2401-2409 (Year: 2021).*

* cited by examiner

APPARATUS AND METHOD FOR DETERMINING TOXIC LOAD QUANTIFIERS

FIELD OF THE INVENTION

The present invention generally relates to the field of toxic loads. In particular, the present invention is directed to an apparatus and method for determining toxic load quantifiers.

BACKGROUND

Many modern products contain toxic chemicals that may impact an individual's wellbeing. However, many individuals are unaware of these toxic chemicals and are therefore uninformed of toxin impacts to their wellbeing when purchasing products.

SUMMARY OF THE DISCLOSURE

In an aspect an apparatus for determining toxic load quantifiers is presented. An apparatus includes at least a processor and a memory communicatively connected to the at least a processor. A memory contains instructions configuring at least a processor to receive user input comprising first user data. At least a processor is configured to generate a query as a function of first user data. At least a processor is configured to obtain at least a query results as a function of a query. At least a processor is configured to determine a toxic load quantifier of at least a query result as a function of a toxicity criterion and first user data. At least a processor is configured to display a toxic load quantifier of at least a query result to a user.

In another aspect a method of determining toxic load rankings using a computing device is presented. A method includes receiving user input at a computing device, wherein the user input comprises first user data. A method includes generating a query as a function of first user data. A method includes obtaining at least a query result as a function of a query. A method includes determining a toxic load quantifier of at least a query result as a function of a toxicity criterion and first user data. A method includes displaying a toxic load quantifier of at least a query result to a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for determining toxic load quantifiers. In an embodiment, an apparatus may be configured to determine a toxic load quantifier of one or more articles of interest.

Aspects of the present disclosure can be used to inform an individual of potential toxic elements that may be effecting their health. Aspects of the present disclosure can also be used to provide recommendations of articles of interest based on user compatibility. This is so, at least in part, because different individuals have different reactions to toxic elements of articles of interest and may have varying compatibility to articles of interest.

Aspects of the present disclosure allow for toxic element reduction in an individual's body. Exemplary embodiments illustrating aspects of the present disclosure are described below in the context of several specific examples.

Figure 1:
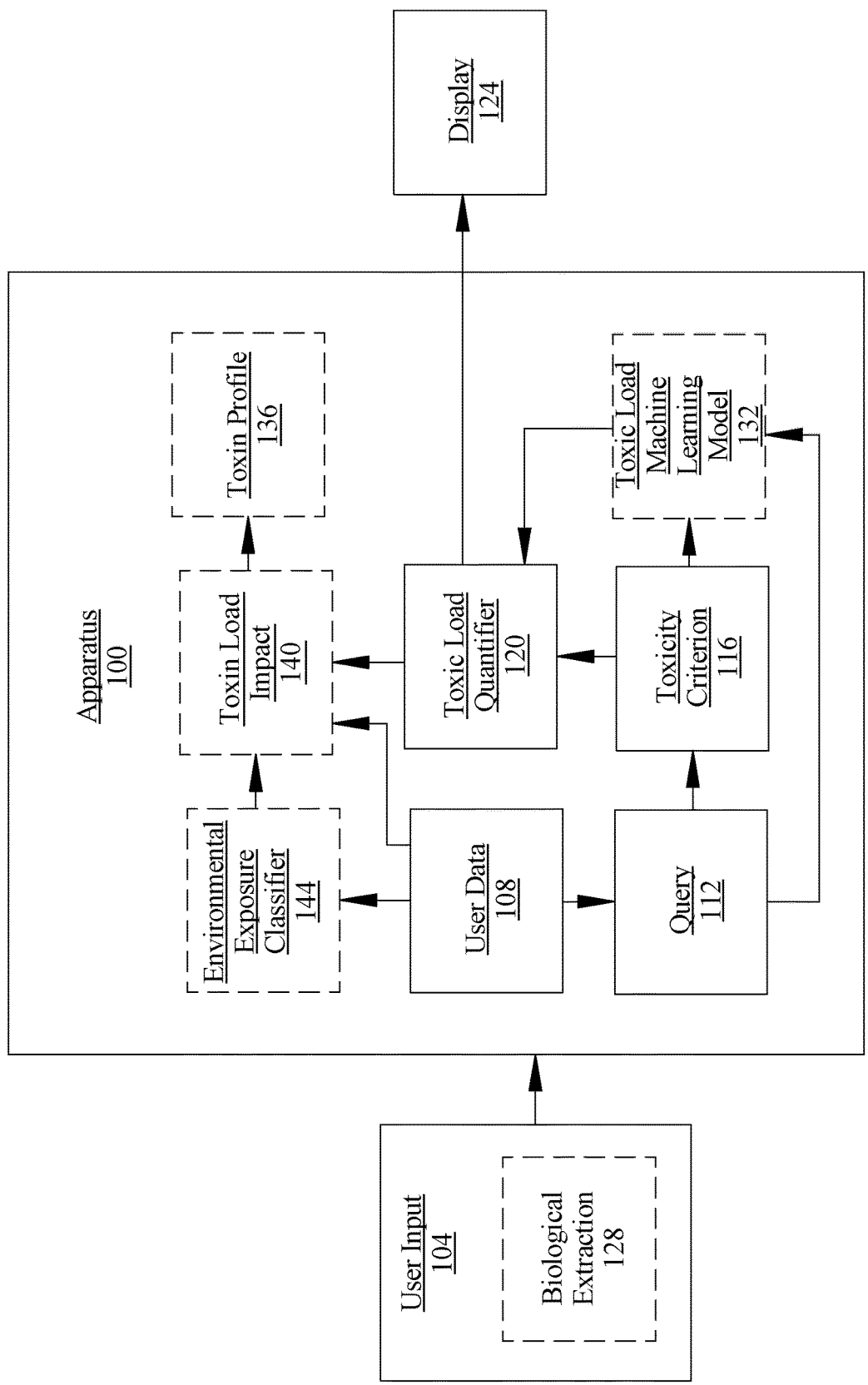
FIG. 1 is an exemplary embodiment of a block diagram of an apparatus for determining toxic loads.

Referring now to FIG. 1, an exemplary embodiment of an apparatus 100 for determining toxic loads is illustrated. Apparatus 100 may include at least a processor and a memory communicatively connected to the at least a processor. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure. A memory may contain instructions configuring the at least a processor to perform various tasks. Apparatus 100 may include any computing device as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of system 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, in some embodiments apparatus 100 may be configured to receive user input 104. "User input" as used in this disclosure is information received from an individual. User input 104 may include, but is not limited to, touch input, text input, voice input, and the like. For instance and without limitation, user input 104 may include an entry of text in a text field of a graphical user interface (GUI) of apparatus 100. In some embodiments, user input 104 may include a biological extraction 128. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DLIEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein estradiol, ferritin folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psycho-logical data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using any machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. Apparatus 100 may receive at least a physiological data from one or more other devices after performance; apparatus 100 may alternatively or additionally perform one or more assessments and/or tests to obtain at least a physiological data, and/or one or more portions thereof, on apparatus 100. For instance, at least physiological data may include or more entries by a user in a form or similar graphical user interface object; one or more entries may include, without limitation, user responses to questions on a psychological, behavioral, personality, or cognitive test. For instance, apparatus 100 may present to a user a set of assessment questions designed or intended to evaluate a current state of mind of the user, a current psychological state of the user, a personality trait of the user, or the like; apparatus 100 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS). Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, and blood clotting factors.

With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile*, *cryptosporidium* species, *Cyclospora cayetanensis*, *Cryptosporidium* EIA, *Dientamoeba fragilis*, *Entamoeba histolytica*, *Escherichia coli*, *Entamoeba histolytica*, *Giardia*, *H. pylori*, *Candida albicans*, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter smithies*' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides vulgates*', *Bacteroides-Prevotella*, Barnesiella species, *Bifidobacterium* longarm, *Bifidobacterium* species, *Butyrivibrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin AlC test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of apparatus 100 or may be a separate device in communication with apparatus 100.

In some embodiments, apparatus 100 may be configured to determine user data 108 from user input 104. "User data" as used in this disclosure is information relating to an individual. User data 108 may include physiological data and/or physiological state data as described above. In some embodiments, user data 108 may include, without limitation, geographical data. "Geographical data" as used in this disclosure is information relating to a location of an entity and/or object. Geographical data may include, but is not limited to, locations, addresses, travel information, travel patterns, and the like. In some embodiments, user data 108 may include, without limitation, diet data. "Diet data" as used in this disclosure is information pertaining to nutrient consumption of an individual. Diet data may include, but is not limited to, quantities of nutrients, types of food items, frequency of consumption of food items, and the like. In some embodiments, diet data may include data of an origin of one or more food items. For instance and without limitation, diet data may include data showing an individual consumes a large iced coffee from a coffee shop every day, such as Starbucks or Dunkin' Apparatus 100 may determine one or more origins of coffee beans used to make the large iced coffee. Diet data may include, but is not limited to, vegetarian, vegan, pescatarian, keto, paleo, and/or other diet types. In some embodiments, user data 108 may include climate data. "Climate data" as used in this disclosure is information pertaining to an environment. Climate data may include, but is not limited to, air quality, temperatures, humidity, precipitation patterns, wind patterns, population levels, population density, pollution levels, and the like. In some embodiments, user data 108 may include exercise data. "Exercise data" as used in this disclosure is information pertaining to physical activity of an individual. Exercise data may include, but is not limited to, physical activity frequency, physical activity intensity, types of physical activity, work-related physical activity, recreational physical activity, and the like. In some embodiments, user data 108 may include purchasing data. "Purchasing data" as used in this disclosure is information pertaining to transactional activity of an individual. Purchasing data may include, but is not limited to, frequency of purchases, types of purchases, quantity of purchases, merchant information, and the like. In some embodiments, user data 108 may include product usage data. "Product usage data" as used in this disclosure is information pertaining to an engagement of an individual with one or more products. Product usage data may include, but is not limited to, types of products, frequency of product usage, amount of product usage, and the like. In some embodiments, user data 108 may include first user data. "First user data" as used in this disclosure is initial user data. In some embodiments, user data 108 may include second user data. "Second user data" as used in this disclosure is user data sequential to a first user data. Apparatus 100 may be configured to receive first user data and/or second user data of user data 108. First user data and/or second user data may include any data of user data 108, without limitation.

With continued reference to FIG. 1, user data 108 may be stored in a user database, such as toxin profile 136, as described in more detail below with reference to FIG. 2. A user database may be implemented, without limitation, as a relational database, a key-value retrieval datastore such as a NOSQL database, or any other form or structure for use as a datastore that a person skilled in the art would recognize as suitable upon review of the entirety of this disclosure.

Still referring to FIG. 1, in some embodiments, user input 104 may include a search for an article of interest. An "article of interest," as used in this disclosure, is any product sought after by an individual. A product may include any material intended for use as an ingredient of a cosmetic product. A product may be composed of one or more chemical compounds. Chemical compounds may include natural sources, synthetic sources, and/or artificial sources. Natural sources may include any chemical compound and/or substance produced by a living organism. Natural sources may include one or more handmake and/or certified organic products. Synthetic sources may include one or more products produced by chemical reactions. Artificial sources may include any humanly contrived products. An article of interest may be intended to be applied externally including but not limited to skin-care creams, lipsticks, eye makeup, facial makeup, body makeup, towelettes, contact lenses, deodorants, creams, lotions, powders, perfumes, bath products, bath oils, body salts, body scrubs, body lotions, body creams, body butters, nail polish, hand sanitizer, hair color, hair spray, hair gel, shampoo, conditioner, sunscreen, lip gloss, lip liner, lip plumper, lip balm, lip stain, lip conditioner, lip primer, lip booster, lip butter, makeup primer, makeup concealer, foundation, face powder, rogue, blush, highlight, bronzer, mascara, eye shadow, eye liner, eyebrow pencils, setting spray, false eyelashes, contouring, cleaners, foaming washes, cleansing oil, toners, facial masks, exfoliants, moisturizers, tools utilized to apply products including foundation brush, concealer brush, blush brush, powder brush, highlight brush, eyeshadow brush, eyeliner brush, lip brush, and the like. An article of interest may include a consumable item, such as, but not limited to, water, soda, energy drinks, coffee, tea, chicken, beef, fish, canned food, fruits, vegetables, and the like. A consumable item may include nutritional supplements such as, but not limited to, vitamins, vitamin pills, vitamin powders, protein shakes, protein powder, and the like. An article of interest may include, without limitation, paint, household cleaners, laundry cleaners, pool cleaners, chewing gum, electronics, dental hygiene products, pet care items, and the like.

With continued reference to FIG. 1, user data 108 may include an article of interest based on a user request from user input 104. Apparatus 100 may determine user data 108 to include an article of interest by receiving a user request from user input 104 such as, but not limited to, from a remote device and/or from input on apparatus 100. A user may inquire about a particular product, such as a specific brand and shade of lipstick. A user may inquire about a class and/or category of articles of interest such as shampoos or hair gels. A user may transmit an article of interest from a remote device to apparatus 100 utilizing any network methodology as described herein. A remote device may include without limitation, a display in communication with apparatus 100, where a display may include any display as described herein. A remote device may include an additional computing device, such as a mobile device, laptop, desktop, computer and the like.

Still referring to FIG. 1, in some embodiments, apparatus 100 may be configured to locate an article of interest through query 112. Apparatus 100 may generate query 112 as a function of user data 108. A "query" as used in this disclosure is a search function that returns data. Apparatus 100 may generate query 112 as a function of a querying criterion. A "querying criterion" as used in this disclosure is a metric constraining a query. A querying criterion may include, without limitation, dates, brand names, categories, semantic elements, and the like. A "semantic element" as used in this disclosure is information pertaining to language. A semantic element may include, but is not limited to, a character, word, phrase, text, symbol, and the like. Query 112 may search through the Internet for semantic elements matching semantic elements of a querying criterion. Query 112 may search through, but is not limited to, web pages, search engines, social media sites, databases, and the like. In some embodiments, query 112 may be generated to search through every page of a website.

Still referring to FIG. 1, generating query 112 may include generating a web crawler function. Query 112 may be configured to search for one or more keywords, key phrases, and the like. A keyword may be used by query 112 to filter potential results from a search. As a non-limiting example, a key phrase may include "Nail Polish". Query 112 may be configured to generate one or more key words and/or phrases as a function of a fuzzy logic system, such as described below with reference to FIG. 4. Query 112 may give a weight to one or more semantic elements of a querying criterion. "Weights", as used herein, may be multipliers or other scalar numbers reflecting a relative importance of a particular attribute or value. A weight may include, but is not limited to, a numerical value corresponding to an importance of an element. In some embodiments, a weighted value may be referred to in terms of a whole number, such as 1, 100, and the like. As a non-limiting example, a weighted value of 0.2 may indicated that the weighted value makes up 20% of the total value. As a non-limiting example, query 112 may include key words of "diet soda". Query 112 may give a weight of 0.8 to the word "soda", and a weight of 0.2 to the word "diet". Weighted values may be tuned through a machine-learning model, such as a machine learning model as described below in FIG. 5. In some embodiments, query 112 may generate weighted values based on prior queries. In some embodiments, query 104 may be configured to filter out one or more "stop words" that may not convey meaning, such as "of," "a," "an," "the," or the like.

Still referring to FIG. 1, in some embodiments, query 112 may include an index classifier. In an embodiment, an index classifier may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. An index classifier may include a classifier configured to input articles of interest and output web search indices. A "web search index," as defined in this disclosure is a data structure that stores uniform resource locators (URLs) of web pages together with one or more associated data that may be used to retrieve URLs by querying the web search index; associated data may include keywords identified in pages associated with URLs by programs such as web crawlers and/or "spiders." A web search index may include any data structure for ordered storage and retrieval of data, which may be implemented as a hardware or software module. A web search index may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a web search index may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a web search index may reflect categories, cohorts, and/or populations of data consistently with this disclosure. In an embodiment, a web search query at a search engine may be submitted as a query to a web search index, which may retrieve a list of URLs responsive to the query. In some embodiments, apparatus 100 may be configured to generate query 112 based on a freshness and/or age of a query result. A freshness may include an accuracy of a query result. An age may include a metric of how outdated a query result may be.

Still referring to FIG. 1, in some embodiments, apparatus 100 may generate query 112 using a language processing module. A language processing module may include any hardware and/or software module. A language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, a language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to FIG. 1, a language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, in some embodiments, apparatus 100 may generate query 112 using optical character recognition or optical character reader (OCR). Optical character recognition (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIG. 5. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIG. 5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of apriori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, a language processing module may use a corpus of documents to generate associations between language elements in a language processing module, and diagnostic engine may then use such associations to analyze words extracted from one or more documents and determine that the one or more documents indicate significance of a category. In an embodiment, language module and/or apparatus 100 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into apparatus 100. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

With continued reference to FIG. 1, apparatus 100 may be configured to identify at least an ingredient contained within an article of interest. Apparatus 100 may identify at least an ingredient contained within an article of interest by evaluating an article of interest to determine a manufacturer. A "manufacturer," as used in this disclosure, is any producer of an article of manufacture, and/or an article of interest and/or ingredients thereof. For example, DOVE DEEP MOISTURE BODY WASH is manufactured by Unilever of London, United Kingdom. In yet another non-limiting example, a VENUS SMOOTH WOMEN'S RAZOR is manufactured by Gillette, of Boston, Massachusetts. Apparatus 100 may determine a current ingredient list contained within an article of interest from a manufacturer. Apparatus 100 may do determine a current ingredient list contained within an article of interest from a manufacturer utilizing any network methodology as described herein. In an embodiment, apparatus 100 may identify ingredients contained within an article of interest such as for example, ONE LOVE ORGANICS VITAMIN B CLEANSING OIL as produced by One Love Organics of St. Simons, Georgia which includes ingredients that include sunflower seed oil, papaya seed oil, and pumpkin seed oil. In an embodiment, one or more ingredients may be stored in an ingredient database located on apparatus 100 as described in more detail below. An ingredient database may be implemented, without limitation, as a relational database, a key-value retrieval datastore such as a NOSQL database, or any other form or structure for use as a datastore that a person skilled in the art would recognize as suitable upon review of the entirety of this disclosure.

Still referring to FIG. 1, apparatus 100 may be configured to determine one or more toxic elements of results of query 112, such as articles of interest. In some embodiments, apparatus 100 may communicate with a toxin database to identify and/or verify one or more toxic elements, toxic element categories, and the like. "Toxic elements" as used in this disclosure are chemicals and/or elements that are detrimental to an individual's wellbeing. Toxic elements may include, but are not limited to, formaldehyde, asbestos, azodicarbonamide, 1,4-dioxane, bisphenol A (BPA), phthalates, volatile organic compounds (VOCs), flame retardants, polyfluoroalkyl substances (PFAS), arsenic, polytetrafluoroethylene, triclosan, dioxins, perfluorinated chemicals (PFCs), atrazine, perchlorate, formaldehyde, chloroform, polybrominated diphenyl ethers (PBDEs), DEET, toluene, nonylphenols, aluminum, lead, mercury, and the like. In some embodiments, a toxic element, such as without limitation a toxic element of toxic element quantifier 120, may include, but is not limited to, carcinogens, heavy metals, and the like. In some embodiments, a toxic element of toxic element quantifier 120 may include, without limitation, one or more toxins that affect a user's immune system, such as dioxin. In some embodiments, a toxic element of toxic element quantifier 120 may include, without limitation, one or more toxins that affect DNA of a user, such as heavy metals, air pollutants, peroxisome proliferators, and the like. In some embodiments, a toxic element of toxic element quantifier 120 may include, without limitation, one or more toxins that affect epigenetics of a user. A toxic element of toxic element quantifier 120 may include toxins that may be specific to a user. For instance and without limitation, toxic elements of toxic element quantifier 120 may have negative effects on a first user's biology, while having little or no effect on a second user's biology. Toxic elements of toxic element quantifier 120 may be specific to a user based on, but not limited to, user biology, user data 108, and the like. User specific toxic elements of toxic element quantifier 120 may be as described in further detail below.

Still referring to FIG. 1, in some embodiments, apparatus 100 may use a toxic element classification model. A "toxic element classification model" as used in this disclosure is a classifier that inputs toxic elements and classifies the toxic elements to one or more toxic element categories and/or subcategories. A toxic element classification model may be trained with training data correlating toxic elements to toxic element categories, such as, but not limited to, heavy metals, pollutants, and the like. Training data may be received from user input, external computing devices, and/or previous iterations of processing. A toxic element classification model may input toxic elements classify the toxic elements to categories such as heavy metals, pollutants, and the like. In some embodiments, a toxic element classification model may input toxic elements, such as toxic elements found in results of query 112, and classify the toxic elements to levels of toxicity. "Levels of toxicity" as used in this disclosure are metrics indicating a degree of harmfulness of an element. Levels of toxicity may include, but are not limited to, not toxic, mildly toxic, moderately toxic, highly toxic, lethal, and the like. In some embodiments, a toxic element classification model may be configured to classify toxic elements to symptom categories. "Symptom categories" as used in this disclosure are groupings of effects of encountering toxic elements. Symptom categories may include, but are not limited to, irritant, nausea, fatigue, dizziness, dry skin, headaches, poor sleep, loss of appetite, and the like. Toxic elements may be classified to multiple categories, with each classification having a score associated therewith. For instance and without limitation, a cigarette may be classified to a toxic element group of "carcinogens" with a score of 10/10, and also be classified to a toxic element group of "heavy metals" with a score of 7/10. In some embodiments, apparatus 100 may generate a cumulative score of a toxic element and/or toxic load quantifier 120 based on one or more score of toxin classification to one or more toxin element groups and/or categories. For instance, a cigarette may have a 10/10 carcinogen score and a 7/10 heavy metals score to amount to a cumulative toxin score of 17/20, or 85 out of 100.

Still referring to FIG. 1, in some embodiments, apparatus 100 may use a toxic element machine learning model. A toxic element machine learning model may be trained with training data correlating articles of interest to toxic elements, toxic groupings, and the like. Training data may be received from user input, external computing devices, and/or previous iterations of processing. A toxic element machine learning model may be configured to input articles of interest and output one or more toxic elements of the articles of interest. For instance and without limitation, an article of interest may include deodorant, and a toxic element machine learning model may input the deodorant and output a toxic element of aluminum chlorohydrate. Apparatus 100 may utilize a toxic element machine learning model to determine one or more toxic elements of articles of interest.

Still referring to FIG. 1, in some embodiments, apparatus 100 may be configured to determine a toxic load of one or more articles of interest. A "toxic load" as used in this disclosure is a quantity of toxic elements of an article of interest. A toxic load may include levels of toxicity as described above. In some embodiments, a toxic load may include, without limitation, high amounts of toxic elements, moderate amounts of toxic elements, low amounts of toxic elements, and the like. In some embodiments, apparatus 100 may determine a toxic load over a period of time for a user. For instance and without limitation, a user may consume four diet sodas everyday which may contain aspartame. Apparatus 100 may determine a high toxic load of the diet sodas. A user may drink one diet soda a day, to which apparatus 100 may determine a low toxic load due to the lower amount of aspartame consumed daily. In some embodiments, apparatus 100 may determine a toxic load based on, but not limited to, absorption rates of toxic elements, ratios of toxic elements to non-toxic elements of articles of interest, frequency of use of toxic elements, and the like. For instance and without limitation, apparatus 100 may determine a high toxic load of tap water that a user may consume multiple times a day. Apparatus 100 may determine a low toxic load for concealer, due to a low adsorption of toxic elements through facial skin of a user. Apparatus 100 may determine a low toxic load for a large watermelon containing trace amounts of pesticide, due to a ratio of toxic elements of pesticide to non-toxic elements of the watermelon. Alternatively, apparatus 100 may determine a high toxic load for a small watermelon with moderate amounts of pesticide due to a ratio of toxic elements of pesticide to non-toxic elements of the watermelon. In some embodiments, apparatus 100 may be configured to utilize toxic load machine learning model 132. Toxic load machine learning model 132 may be trained with training data correlating articles of interest to toxic loads. Training data may be received through user input, external computing devices, and/or previous iterations of processing. In some embodiments, toxic load machine learning model 132 may be configured to input articles of interest and output one or more toxic loads.

With continued reference to FIG. 1, apparatus 100 may generate a clustering algorithm utilizing biological training data to generate a biological model. A "clustering algorithm," as used in this disclosure, is any process and/or calculation that involves grouping a set of objects and/or data in a way that objects and/or data in the same group or cluster are more similar to each other than to those in other groups or clusters. Clustering algorithm may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like.

With continued reference to FIG. 1, apparatus 100 may generate a clustering algorithm utilizing biological training data. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, "biological training data," as used in this disclosure, is training data that includes a plurality of biological extractions 128 and a plurality of correlated articles of interest. Apparatus 100 may utilize a clustering algorithm and biological training data to generate a biological model. A "biological model," as used in this disclosure is a machine-learning model that utilizes user data 108 as an input and outputs a biological user profile. Generating a biological model may include performing a series of one or more calculations, algorithms, and/or equations. Apparatus 100 may determine an article of interest using a biological model. For example, apparatus 100 may utilize user data 108, such as without limitation biological extraction 128 of a user that shows the user has high urinary levels of heavy metals such as lead and mercury in combination with generating biological model utilizing biological training data to determine an article of interest such as a shampoo that does not contain heavy metals including lead and mercury, and that also does not contain any precursors to heavy metals. In some embodiments, a biological model may be configured to determine a toxin baseline of a user. A "toxin baseline" as used in this disclosure is an average quantity of toxic elements in an individual's body. A toxin baseline may include average levels of, but not limited to, heavy metals, plastics, sweeteners, and the like. In some embodiments, a biological model may be configured to predict a change in toxicity levels of a user as a function of a toxic load of articles of interest.

With continued reference to FIG. 1, apparatus 100 may generate query 112 to locate an article of interest of user data 108. Apparatus 100 may generate query 112 to locate an article of interest based on climate data of where a user is currently located and/or where a user currently resides. Apparatus 100 may determine an element of user climate data of user data 108 from user input 104, which may be received from a remote device. An "element of user climate data," as used in this disclosure, is any data describing weather conditions prevailing in an area in general where a user resides, spends time working, commutes to and from and the like. An element of user climate data may describe the average temperature, humidity, atmospheric pressure, wind, and/or precipitation in a specific geographical location. For instance and without limitation, a user who resides in Hawaii may generate an element of user climate data that describes moderate temperatures that range between 70 degrees Fahrenheit and 90 degrees Fahrenheit year round with moderate humidity. In yet another non-limiting example, a user who resides in Portland, Maine may generate an element of user climate data that describes dry winters with temperatures that do not exceed 40 degrees Fahrenheit on average, and wet humid summers that see moderate rainy precipitation with temperatures that do not exceed 85 degrees Fahrenheit on average. In an embodiment, an element of user climate data may include an element of user geolocation data that may be utilized by apparatus 100 to determine an element of user climate data. An "element of user geolocation," as used in this disclosure, is an identification of a real-world geographical location of a user. An element of user geolocation data may be obtained from a radar source, a remote device such as a mobile phone, and/or internet connected device location. An element of user geolocation may include a global positioning system (GPS) of a user. An element of user geolocation may include geographic coordinates that may specify the latitude and longitude of a particular location where a user is located.

With continued reference to FIG. 1, apparatus 100 may locate an article of interest based on articles of interest that may be available for a user to purchase within a certain geolocation of the user. Apparatus 100 may receive an element of user geolocation data from a remote device. An element of user geolocation data may include any of the elements of user geolocation data as described above. Apparatus 100 may identify articles of interest available to be acquired within a user geolocation. Articles of interest within the user geolocation may include a component, set of components, or system that enables apparatus 100 to detect articles of interest within a certain radius of the user geolocation, within a certain geographic location of the user, within the metes and bounds of a local, municipal, state, political, and/or geographical region. Articles of interest may be available to be acquired if they are available to be purchased and/or delivered to the user within the user geolocation. Apparatus 100 may determine items are available to be purchased and/or delivered to the user within the user geolocation by receiving inputs using any network methodology as described herein. Information regarding availability of articles of interest that may be available to be acquired may be updated in real time. Apparatus 100 may select an article of interest after identifying articles of interest available to be acquired within the user geolocation. For example, apparatus 100 may receive a transmission from a remote device indicating that a user resides in Tampa, Florida. Apparatus 100 may identify articles of interest available to be acquired within Tampa, Florida such as for example a locally made perfume native to the Tampa, Florida area. Apparatus 100 may select the perfume as an article of interest.

With continued reference to FIG. 1, apparatus 100 may locate an article of interest based on user input 104. Apparatus 100 may include display 124. A "display" as used in this disclosure is a device configured to show data. Display 124 may include, but is not limited to, smartphone screens, laptop screens, monitors, and the like. In some embodiments, display 124 may include a graphical user interface. A graphical user interface may include without limitation a form or other graphical element having display fields, where one or more elements of information may be displayed. A graphical user interface may include sliders or other use inputs that may permit a user to indicate relative and/or absolute importance of a particular article of interest. Apparatus 100 may display on a graphical user interface of display 124 a plurality of conditional complaints. A "conditional complaint," as used in this disclosure, is a description of any problem that use of an article of interest is intended to correct. A conditional complaint may include a description of a condition on the skin such dry skin or redness upon waking. A conditional complaint may include a description of a particular nail polish or eye shadow shade that a ser may considering using. A conditional complaint may include a description of an issue relating to one's hair such as fizziness experienced during blow-drying. A conditional complaint may include a description of a seasonal issue such as oiliness experienced in the T zone or itchy skin on one's hands in the winter. Apparatus 100 may receive a user entry selecting at least a conditional complaint. In an embodiment, a user may select, using a slide on a graphical user interface, a particular conditional complaint. In an embodiment, a user may select several conditional complaints that may pertain to the user. Apparatus 100 may display on a graphical user interface of display 124 a plurality of articles of interest associated with a selected conditional complaint. For example, a selected conditional complaint such as itchy skin on face may prompt graphical user interface to display on display 124 articles of interest intended to correct itchy skin on face, including a moisturizer, a hydrocortisone cream, and a cucumber cooling gel. Apparatus 100 may receive a user entry selecting an article of interest from a plurality of articles of interest.

With continued reference to FIG. 1, apparatus 100 may be configured to generate an ingredient metabolic classifier using ingredient training data. "Ingredient training data," as used in this disclosure, is training data that includes a plurality of user data 108 and a plurality of correlated ingredient metabolic profiles. An "ingredient metabolic profile," as used in this disclosure, is a collection of indicators as to a user's ability to absorb, and metabolize one or more ingredients and/or articles of interest, and/or topically effect a user's skin. Indicators may include any marker of chemical absorption, distribution, metabolism, and/or elimination, including for example an indicator of liver function, kidney function, gut function, and the like. Indicators may include topical effects such as the ability of one or more ingredients and/or articles of interest to cause an allergy, sensitivity, effect on a skin's microbiome population and the like. An "ingredient," as used in this disclosure, includes any component of an article of interest. An ingredient may include an active ingredient that may be biologically active and/or affect the therapeutic action of the article of interest. An ingredient may include a non-active ingredient which may include a component of an article of interest that does not affect the therapeutic action of the article of interest. In an embodiment, a non-active ingredient may include an inert ingredient that may include for example, a binding material, dye, preservative, and/or flavoring agent. In an embodiment, an ingredient may be the same as the article of interest. For example, an article of interest such as red nail polish may include several ingredients including nitrocellulose, chromium oxide, mica, and thixotropy. In yet another non-limiting example, an article of interest such as a hydrating serum may include water, glycerin, hydrolyzed hazelnut protein, carrageenan, and punica granatum. In an embodiment, an ingredient metabolic profile may indicate that a user has compromised hepatic function and as such an ingredient such as parabens will be toxic when used in a hair-styling product but not when applied in a small amount in nail polish. In yet another non-limiting example, an ingredient metabolic profile may indicate that a user has super-functioning liver and kidney function, and as such an ingredient such as phthalates contained within any article of interest including for example shampoo, conditioner, hair gel, and body lotion will be adequately metabolized by the user.

With continued reference to FIG. 1, apparatus 100 may generate an ingredient metabolic classifier. An "ingredient metabolic classifier," as used in this disclosure, is a machine-learning model that sorts inputs into categories or bins of data using a classification algorithm. An ingredient metabolic classifier may utilize a user data 108 as an input and outputs an ingredient metabolic profile. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, an ingredient metabolic classifier may generate an ingredient metabolic profile that may contain a plurality of ingredients containing a metabolic impact label. A "metabolic impact label," as used in this disclosure is any indication as to the safety of use of an ingredient. A metabolic impact label may indicate if a user should never use an ingredient, sparingly use an ingredient, use an ingredient, and the like. For example, a user with heavy metal toxicity may receive a metabolic impact label that indicates the user should never use an article of manufacture that contains parabens. A metabolic impact label may indicate if a user can occasionally use an article of manufacture that contains a particular ingredient. For example, a metabolic impact label may indicate that a user can use an ingredient such as benzene contained within certain articles of interest such as those applied to the nails and hair but the user should not use benzene contained within any product being applied to the face or skin. A metabolic impact label may indicate the frequency with which a user may apply an ingredient, for example a metabolic impact label may indicate that a user may apply a lotion containing coconut oil no more than once per day. In an embodiment, a metabolic impact label may indicate that a user can frequently use an article of manufacture.

With continued reference to FIG. 1, apparatus 100 may be configured to determine toxic load impact 140 of an article of interest. A "toxic load impact" as used in this disclosure, is an indication of the degree to which an article of interest may impact a toxin load of a user. Toxic load impact 140 may refer to a degree and/or frequency that an article of interest may be tolerated by a user. Tolerability may indicate how compatible an article of interest is with a user's body. For example, apparatus 100 may determine that an article of interest is best tolerated if used no more than three days each week. In yet another non-limiting example, apparatus 100 may determine that an article of interest is not tolerated but another article of interest may be better suited. Apparatus 100 may determine toxic load impact 140 and/or tolerability of an article of interest using a metabolic profile and at least an ingredient contained within the article of interest. Apparatus 100 may compare at least an ingredient contained within an article of interest to a metabolic profile to determine a tolerability of the article of interest. For example, apparatus 100 may determine that an article of interest, such as a body lotion, will be tolerated by a user and/or have a low toxic load impact because each of the three ingredients are listed within a metabolic profile as being compatible for the user. In yet another non-limiting example, apparatus 100 may determine that an article of interest will not be tolerated by a user and/or may have a high toxic load impact because the article of interest contains an ingredient such as isopropyl alcohol, which the user is unable to tolerate. In yet another non-limiting example, apparatus 100 may determine that an article of interest, such as a shampoo, will be tolerated by the user if used no more than three times each week because the shampoo contains an ingredient such as sodium lauryl sulfate which the user's ingredient metabolic profile indicates as being tolerated and/or having a moderate toxic load impact in controlled doses and not exceeding daily usage.

With continued reference to FIG. 1, apparatus 100 may use one or more machine-learning algorithms to determine toxic load impact 140 and/or tolerability. Apparatus 100 may generate a tolerability machine-learning model to determine tolerability. A "tolerability machine-learning model," as used in this disclosure, is a machine-learning model that utilizes a metabolic profile as an input and outputs a plurality of articles of interest tolerability labels. An "article of interest tolerability label," as used in this disclosure, is an indicator as to the tolerability of a particular article of interest. An article of interest tolerability label may include textual data. Tolerability includes any of the measures of tolerability as described above. For example, an article of interest 108 tolerability label may indicate that an article of interest such as BIG APPLE RED OIL NAIL LACQUER as produced by OPI Products of North Hollywood, California is not tolerated by a user because it contains red dyes which the user is unable to metabolize, but NUDE OIL NAIL LACQUER as produced by OPI Products of North Hollywood, California is tolerated by the user because it does not contain red dyes. Apparatus 100 may generate a tolerability machine-learning model which may include performing a series of one or more calculations, algorithms, and/or equations. Apparatus 100 may output a plurality of articles of interest tolerability labels utilizing a tolerability machine-learning model. Apparatus 100 may determine a tolerability of an article of interest using a plurality of output articles of interest tolerability labels. Apparatus 100 may utilize output articles of interest tolerability labels to suggest other articles of interest that may be better tolerated and/or better suited for a user.

Still referring to FIG. 1, in some embodiments, apparatus 100 may be configured to generate a prophylaxis protocol. A prophylaxis protocol may be generated as a function of a toxic element, toxic load impact 140, and the like. A "prophylaxis protocol" as used in this disclosure is a process of negating toxic effects. For instance and without limitation, a prophylaxis protocol may identify shampoo as an article of interest. A prophylaxis protocol may include taking a demethylate to reduce damage done to DNA of a user. Apparatus 100 may use any machine learning model, classifier, and/or fuzzy logic system as described throughout this disclosure to generate a prophylaxis protocol, without limitation. A prophylaxis protocol may be generated as a function of a detoxing protocol as described below.

Still referring to FIG. 1, apparatus 100 may be configured to generate a cumulative toxin exposure model. A "cumulative toxin exposure model" as used in this disclosure is a mapping of toxin exposures over a period of time. A cumulative toxin exposure model may be determined as a function of toxic load impact 140, toxic element, and/or other forms of toxic exposure. In some embodiments, a cumulative toxic exposure model may e configured to input user data 108 and output a toxin exposure score. For instance and without limitation, a toxic exposure score may include an average toxin exposure over a period of time, categories of toxin exposures over a period of time, trends of toxin exposure, and the like. A cumulative toxin exposure model may be generated through any machine learning model and/or classifier as described throughout this disclosure, without limitation.

Still referring to FIG. 1, apparatus 100 may be configured to generate a detoxing protocol. A "detoxing protocol" as used in this disclosure is a process of lowering a cumulative level of toxins. A detoxing protocol may include, without limitation, avoiding environmental toxins, consuming dietary supplements, using chemical-free articles of interest, adjusting a diet, and the like. A detoxing protocol may be generated through any machine learning model and/or classifier as used throughout this disclosure, without limitation. In some embodiments, apparatus 100 may update a detoxing protocol as a function of receiving second user data of user data 108. For instance and without limitation, first user data of user data 108 may show increased levels of toxins, to which a detoxing protocol may be generated to reduce the increased levels of toxins. Second user data of user data 108 may be received after a period of time from an initial engagement with a detoxing protocol. Second user data of user data 108 may show reduced levels of toxins in a user's system, to which a detoxing protocol may be updated accordingly. This process may be repeated indefinitely and/or until a toxin level is reached.

With continued reference to FIG. 1, apparatus 100 may make alternative recommendations and/or suggestions for an article of interest when an article of interest is not tolerated by a user. Apparatus may determine that an article of interest is not tolerable for a user. This may be performed utilizing any of the methodologies as described above. Apparatus 100 may identify a class category of an article of interest that is not tolerable for a user. A "class category," as used in this disclosure, is a collection of one or more articles of interest that have shared characteristics. Shared characteristics may include similar purposes, similar uses, similar functions, similar characteristics and the like. For example, a class category may include nail polish, hair styling products, shaving products, makeup, products intended for women, products intended for men, parfum, cologne, anti-perspirants, deodorants, skin care products, soaps, and the like. Apparatus 100 may identify a class category such as by consulting an ingredient database. In an embodiment, articles of interest may be listed within an ingredient database by class category. Apparatus 100 may locate an article of interest contained within a class category that is tolerable for a user. Apparatus 100 may locate an article of interest contained within a class category by consulting an ingredient database. Apparatus 100 may select an article of interest that is tolerable for a user by utilizing an article of interest tolerability label. For example, apparatus 100 may determine that an article of interest, such as an apricot face wash, is not tolerable for a user based on an article of interest tolerability label. In such an instance, apparatus 100 may identify the apricot face wash as belonging to a class category of being a face wash, and as such locate an article of interest such as a mango face wash that is tolerable for a user based on an article of interest tolerability label. Apparatus 100 may suggest the mango face wash instead, such as by transmitting the suggestion of the mango face wash to a remote device and/or by displaying the mango face wash on a graphical user interface through display 124 for a user.

Still referring to FIG. 1, in some embodiments, apparatus 100 may be configured to compare query results, such as articles of interest, to toxic criterion 116. A "toxic criterion" as used in this disclosure is a metric of a toxic element constraining a selection. Toxic criterion 116 may include, but is not limited to, amounts of toxic elements, types of toxic elements, toxicity levels of toxic elements, and the like. Toxic criterion 116 may be determined through user data 108 and/or user selection. For instance and without limitation, a user may request a fragrant-free shampoo. Apparatus 100 may determine toxic criterion 116 to include "no fragrance" and generate query 112 to find a fragrant-free shampoo, and compare query results to toxic criterion 116 to find a best result. In some embodiments, apparatus 100 may determine toxic criterion 116 based on user data 108, such as, without limitation, symptomatic data received from user input 104. For instance and without limitation, user data 108 may include a symptom of fatigue and an article of interest of deodorant. Apparatus 100 may determine toxic criterion 116 to include low levels of fatigue-inducing elements, such as, without limitation, heavy metals. Apparatus 100 may generate query 112 to search for deodorants, and compare results of query 112 to toxic criterion 116 to find a deodorant without fatigue-inducing elements, such as heavy metals. In some embodiments, apparatus 100 may use a toxic criterion machine learning model to determine toxic criterion 116. A toxic criterion machine learning model may be trained with training data correlating one or more elements of user data 108 to toxic criterion 116. Training data may be received through user input, external computing devices, and/or previous iterations of processing. In some embodiments, a toxic criterion machine learning model may be configured to input user data 108 and output toxic criterion 116. For instance and without limitation, a toxic criterion machine learning model may input user data 108, which may include self-reported symptom data such as nausea, and output toxic criterion 116 of low levels of nausea-inducing toxic elements, such as without limitation aspartame.

Still referring to FIG. 1, apparatus 100 may be configured to compare results of query 112 with toxicity criterion 116 by generating an objective function. An "objective function"

as used in this disclosure is a process of minimizing or maximizing one or more values based on a set of constraints. Apparatus 100 may generate an objective function to optimize a matching of articles of interest to toxic criterion. In some embodiments, an objective function of apparatus 100 may include an optimization criterion. An optimization criterion may include any description of a desired value or range of values for one or more elements of a toxic criterion; desired value or range of values may include a maximal or minimal value, a range between maximal or minimal values, or an instruction to maximize or minimize a toxic criterion. As a non-limiting example, an optimization criterion may specify that articles of interest should be within a 1% difference of a toxic criterion; an optimization criterion may cap a difference of an article of interest and a toxic criterion, for instance specifying that an article of interest must not have a difference from a toxic criterion greater than a specified value. An optimization criterion may specify one or more tolerances for differences in toxic criterion. An optimization criterion may specify one or more desired toxic criteria for a matching process. In an embodiment, an optimization criterion may assign weights to different toxic criterion or values associated with toxic criterion; weights, as used herein, may be multipliers or other scalar numbers reflecting a relative importance of a particular attribute or value. One or more weights may be expressions of value to a user of a particular outcome, toxic criterion value, or other facet of a matching process; value may be expressed, as a non-limiting example, in remunerative form, such as a cost of an article of interest, a cost of treating symptoms of toxic elements, or the like. As a non-limiting example, minimization of a cost of an article of interest may be multiplied by a first weight, while tolerance above a certain value may be multiplied by a second weight. Optimization criteria may be combined in weighted or unweighted combinations into a function reflecting an overall outcome desired by a user; function may be a toxic criterion feature function to be minimized and/or maximized. Function may be defined by reference to toxic criteria constraints and/or weighted aggregation thereof as provided by apparatus 100; for instance, a toxic feature function combining optimization criteria may seek to minimize or maximize a function of toxic criterion feature matching.

Still referring to FIG. 1, apparatus 100 may use an objective function to compare articles of interest with toxic criterion 116. Generation of an objective function may include generation of a function to score and weight factors to achieve an article of interest score for each feasible pairing. In some embodiments, pairings may be scored in a matrix for optimization, where columns represent articles of interest and rows represent toxic criterion potentially paired therewith; each cell of such a matrix may represent a score of a pairing of the corresponding article of interest to the corresponding toxic criterion. In some embodiments, assigning a predicted process that optimizes the objective function includes performing a greedy algorithm process. A "greedy algorithm" is defined as an algorithm that selects locally optimal choices, which may or may not generate a globally optimal solution. For instance, apparatus 100 may select pairings so that scores associated therewith are the best score for each toxic criterion match and/or for each article of interest. In such an example, optimization may determine the combination of toxic criterion matches such that each article of interest pairing includes the highest score possible.

Still referring to FIG. 1, an objective function may be formulated as a linear objective function. Apparatus 100 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all articles of interest r, S is a set of all toxic criterion s, $c_{rs}$ is a score of a pairing of a given article of interest with a given match, and $x_{rs}$ is 1 if an article of interest r is paired with a toxic criterion s, and 0 otherwise. Continuing the example, constraints may specify that each toxic criterion is assigned to only one article of interest, and each article of interest is assigned only one toxic criterion. Articles of interest and toxic criterion may include articles of interest and toxic criterion 116 as described above. Sets of articles of interest may be optimized for a maximum score combination of all generated articles of interests. In various embodiments, apparatus 100 may determine a combination of toxic criterion that maximizes a total score subject to a constraint that all toxic criterion are paired to exactly one article of interest. Not all articles of interest may receive a toxic criterion pairing since each article of interest may only produce one toxic criterion. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on apparatus 100 and/or another device, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, apparatus 100 may assign variables relating to a set of parameters, which may correspond to score articles of interest as described above, calculate an output of mathematical expression using the variables, and select a pairing that produces an output having the lowest size, according to a given definition of "size," of the set of outputs representing each of plurality of candidate article of interest combinations; size may, for instance, included absolute value, numerical size, or the like. Selection of different loss functions may result in identification of different potential pairings as generating minimal outputs. Objectives represented in an objective function and/or loss function may include minimization of toxic elements. Objectives may include minimization of cost of articles of interest. Objectives may include minimization of symptoms associated with articles of interest.

Still referring to FIG. 1, apparatus 100 may be configured to generate toxic load quantifier 120 as a function of user data 108 and/or toxicity criterion 116. A "toxic load quantifier" as used in this disclosure is a quantitative value that indicates a degree of toxicity of a query result with respect to a toxicity criterion. Toxic load quantifier 120 may include a value such as, but not limited to, out of 10, out of 5, and the like. For instance and without limitation, toxic load quantifier 120 may include a 5 star based ranking, with 0 starts as a lowest ranking and 5 starts as a highest ranking. Apparatus 100 may use an objective function as described above to provide toxic load quantifier 120 to one or more articles of interest. Toxic load quantifier 120 may be based on toxicity criterion 116. In some embodiments, apparatus 100 may be configured to reassign articles of interest toxic load quantifier 120 as a function of different toxicity criterion 116. For instance and without limitation, toxicity criterion 116 may include no heavy metals, to which a plurality of articles of inters may be assigned a toxic load quantifier 120. A user may specify a different toxicity criterion 116 of no aspartame, to which apparatus 100 may reassign toxic load quantifier 120 to a plurality of articles of interest. In some embodiments, apparatus 100 may be configured to use a fuzzy logic system to generate toxic load quantifier 120, such as described below with reference to FIG. 4. Apparatus 100 may utilize a toxic load quantifier machine learning model. A toxic load quantifier machine learning model may be trained with training data correlating articles of interest and toxicity criterion 116 to toxic load quantifiers 120. Training data may be received through user input, external computing devices, and/or previous iterations of processing. A toxic load quantifier machine learning model may be configured to input articles of interest, user data 108, and/or toxicity criterion 116, and output toxic load quantifier 120 for one or more articles of interest.

Still referring to FIG. 1, in some embodiments, apparatus 100 may be configured to provide toxic load quantifier 120 to a user through display 124. In some embodiments, apparatus 100 may be configured to generate one or more prompts through display 124 for a user to answer. One or more prompts may be generated on a graphical user interface and/or other form of display 124 for a user to engage with. Prompts may include, without limitation, questions pertaining to physical and/or psychological wellbeing, eating habits, location habits, work habits, and the like. User input 104 may include answers to one or more prompts, which apparatus 100 may determine user data 108 from. For instance and without limitation, apparatus 100 may generate a prompt of "how many x-rays have you had in the last 6 months?" to which a user may answer "5". Apparatus 100 may determine user data 108 to include a high amount of x-ray exposure. In some embodiments, apparatus 100 may be configured to generate a prompt for a user to answer pertaining to potential toxic exposures. A "toxic exposure" as used in this disclosure is an encounter with an element detrimental to an individual's health. Toxic exposure may include, but is not limited to, exposure to x-rays, mercury fillings, cosmetic implants, and the like. For instance and without imitation, apparatus 100 may generate a prompt asking, "How many mercury fillings do you have?" to which a user may answer "3". Apparatus 100 may determine user data 108 to include high levels of mercury from mercury leeching. In some embodiments, toxic exposure may include exposure to one or more environmental elements. "Environmental elements" as used in this disclosure are metrics pertaining to a user's surroundings. Environmental elements may include, but are not limited to, chemicals in drinking water, nearby waste disposal pollution, air pollution, and the like. For instance and without limitation, apparatus 100 may determine a user resides near a golf course. A golf course may pollute a surrounding area from one or more pesticides. Apparatus 100 may determine amounts and/or severity of pollution from a golf course, such as through, but not limited to, searching through databases online to find types and quantities of pesticide the golf course uses. Apparatus 100 may be configured to determine one or more exposures to one or more environmental elements. Environmental elements may include a job type, as described below. In some embodiments, apparatus 100 may classify environmental exposures to toxic element exposure levels using environmental exposure classifier 144. Environmental exposure classifier 144 may be trained with training data classifying environmental elements and/or environmental exposure to toxic element exposure levels. Training data may be received through user input, external computing devices, and/or previous iterations of processing. Environmental exposure classifier 144 may input environmental elements and/or exposures to environmental elements and output toxic element exposure levels.

In some embodiments, and still referring to FIG. 1, apparatus 100 may be configured to generate a prompt asking a user about their job, such as without limitation location of job, job type, travelling associated with a job, and the like. Apparatus 100 may determine one or more toxic elements associated with a job of a user. For instance and without limitation, apparatus 100 may generate a prompt asking, "what is your occupation?" to which a user may answer "miner". Apparatus 100 may determine a toxic element of uranium, radon, diesel exhaust, and the like. Apparatus 100 may determine toxic elements of a plurality of jobs, such as, but not limited to, hairdressing jobs, plastics manufacturing jobs, painting jobs, nail salon jobs, construction jobs, mechanic jobs, agricultural jobs, and the like. In some embodiments, apparatus 100 may be configured to use a job machine learning model to determine one or more toxic elements associated with one or more jobs. A job machine learning model may be trained with training data correlating jobs to toxic elements. Training data may be received through user input, external computing devices, and/or previous iterations of processing. A job machine learning model may be configured to input job types and output one or more toxic elements associated with the job types. For instance and without limitation, a job machine learning model may input "rubber manufacturer" as a job type and output "myriad chemicals" as a toxic element. Apparatus 100 may use a job classifier to classify jobs to toxic element exposure levels, toxic element groupings, toxic element severity, and the like. A job classifier may be trained with training data correlating job types to categories of toxic elements. Training data may be received through user input, external computing devices, and/or previous iterations of processing. Apparatus 100 may use a job classifier to input job types and output toxic element categories, such as, but not limited to, types of toxic elements, exposure levels of toxic elements, severity of toxic elements, and the like. For instance and without limitation, a job classifier may input a job type of "mechanic" and classify the mechanic job type to a low toxic level exposure category, asbestos toxic element grouping, and/or moderate toxic element severity.

Still referring to FIG. 1, in some embodiments, apparatus 100 may be configured to generate a prompt asking for symptoms a user may be suffering from. For instance and without limitation, a user may answer with symptoms such as headaches, dizziness, confusion, nausea, diarrhea, skin irritability, poor eyesight, loss of appetite, and the like. Apparatus 100 may determine potential toxic elements as a function of user data 108. For instance and without limitation, a user input 104 may include user data 108 of a dizziness symptom. Apparatus 100 may determine a potential toxic element may include carbon monoxide poisoning. In some embodiments, apparatus 100 may use a potential toxic element machine learning model to determine potential toxic elements. A potential toxic element machine learning model may be trained with training data correlating symptoms to potential toxic elements. Training data may be received through user input, external computing devices, and/or previous iterations of processing. A potential toxic element machine learning model may input one or more elements of user data 108, such as symptom data, and output potential toxic elements a user may be in contact with. In some embodiments, apparatus 100 may use a fuzzy logic system to determine one or more potential toxic elements a user may be in contact with. For instance and without limitation, a fuzzy logic system of apparatus 100 may determine that if user data 108 includes "user resides by golf course"" and "user has symptoms of fatigue" then the fuzzy logic system may determine an output of "potential golf course pesticide poisoning". A fuzzy logic system may be as described below with reference to FIG. 4.

Figure 2:
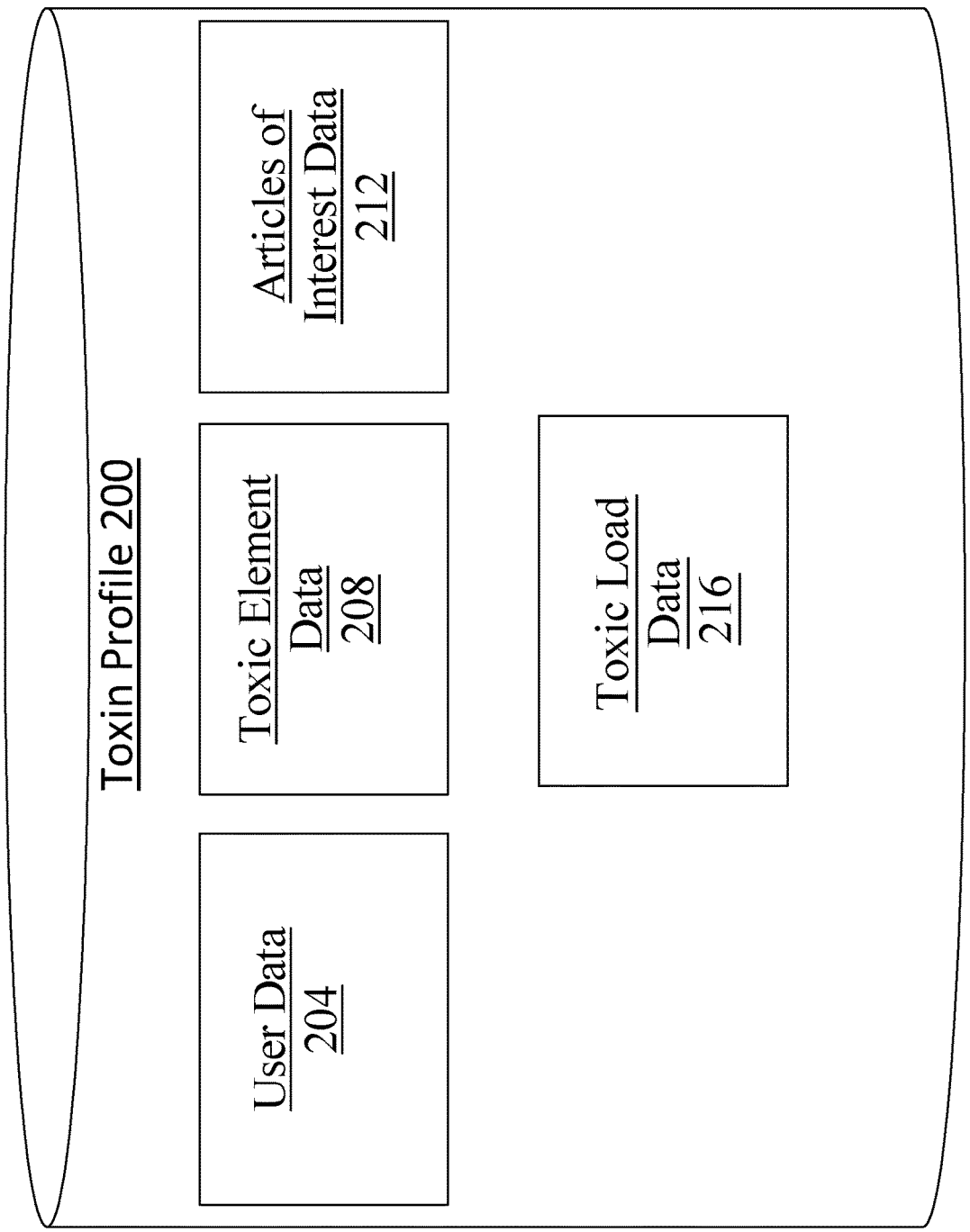
FIG. 2 is an exemplary embodiment of a toxin profile database.

Referring now to FIG. 2, an exemplary embodiment of a toxin profile 200 is presented. Toxin profile 200 may include toxin profile 136 as described above with reference to FIG. 1. Toxin profile 200 may be include a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 2, in some embodiments, toxin profile 200 may include user data 204. User data 204 may include, but is not limited to, diet data, geographical data, exercise data, product usage data, product purchasing data, and the like. User data 204 may include user data 108 as described above with reference to FIG. 1.

Still referring to FIG. 2, in some embodiments, toxin profile 200 may include toxic element data 208. Toxic element data 208 may include one or more toxins a user may be in contact with. In some embodiments, toxic element data 208 may include, without limitation, sources of toxic elements, amounts of toxic elements, types of toxic elements, and the like.

Still referring to FIG. 2, in some embodiments, toxin profile 200 may include articles of interest data 212. Articles of interest data 212 may include, but is not limited to, types of articles of interest, quantities of articles of interest, frequency of usage of articles of interest, and the like. Articles of interest may be as described above with reference to FIG. 1.

Still referring to FIG. 2, in some embodiments, toxin profile 200 may include toxic load data 216. Toxic load data 216 may include, but is not limited to, levels of toxic loads, user baselines of toxic loads, predicted changes in toxic loads, levels of toxic loads associated with toxic elements, and the like. Toxic load data 216 may be updated based on articles of interest data 212, toxic element data 208, and/or user data 204.

Figure 3:
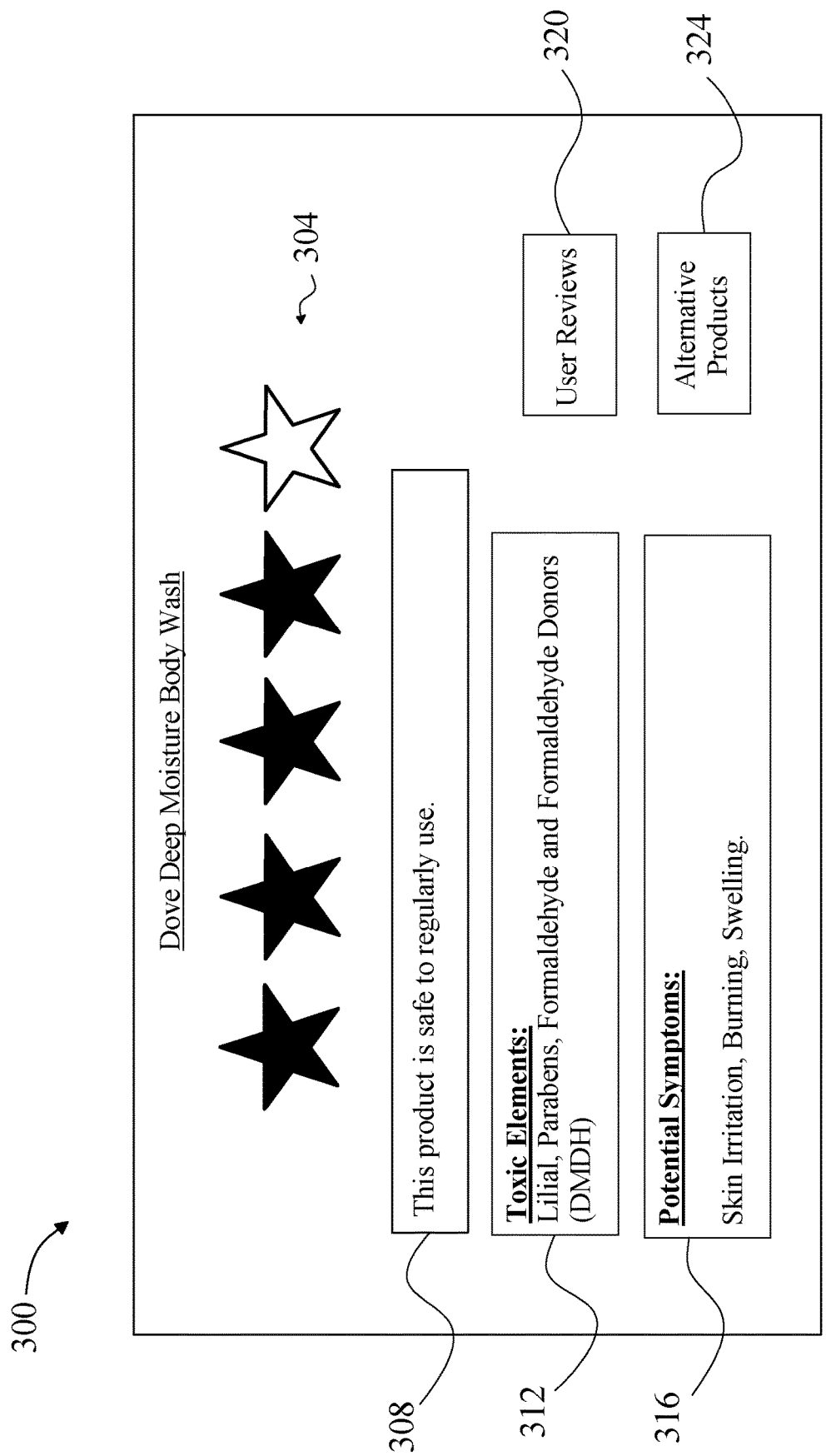
FIG. 3 is an exemplary embodiment of a graphical user interface for toxic load quantifiers.

Referring now to FIG. 3, an exemplary embodiment of a graphical user interface (GUI) 300 for toxic load quantifiers is presented. GUI 300 may include one or more computer icons, elements, and the like. In some embodiments, GUI 300 may include one or more interactable items. An "interactable item" as used in this discourse is a graphical element configured to change an attribute based on a user input. Interactable icons may include, but are not limited to, slide bars, search bars, buttons, text fields, scroll bars, refresh buttons, and the like. In some embodiments a user may enter a search for an article of interest in a search field of GUI 300. GUI 300 may be configured to display one or more articles of interest to a user based on, but not limited to, toxic load quantifiers, toxic elements, costs, delivery times, and the like. In some embodiments, GUI 300 may be configured to present articles of interest to a user based on previous searches, user data such as toxic load levels and/or other biological elements, reaction severity to toxic elements, and the like. Apparatus 100 may be configured to use any machine learning model, classifier, and/or fuzzy logic system as described in this disclosure, without limitation, to provide a user with recommendations of articles of interest through GUI 300.

Still referring to FIG. 3, in some embodiments, GUI 300 may be configured to provide toxic load quantifier 304. Toxic load quantifier 304 may include toxic load quantifier 120 as described above with reference to FIG. 1. Toxic load quantifier 304 may include, without limitation, a ranking out of five starts, out of a scale of 1-10, a percentage score, and the like. In some embodiments, toxic load quantifier 304 may include an alphabetic score, such as, but not limited to, "A+", "A", "A−", "B+", "B", "B−", "C+", "C", "C−", "D+", "D", "D−", "F", and the like. In some embodiments, GUI 300 may include summary statement 308. Summary statement 308 may include guidance on a usage of an article of interest. For example, and without limitation, summary statement 308 may read "this product is safe to regularly use", "this product is ok to use in moderation", "use this product sparingly", "do not use this product", and the like. In some embodiments, summary statement 308 may provide a reasoning for guidance on a usage of an article of interest. As a non-limiting example, summary statement 308 may read "based on your biological toxin profile, this product is safe to use regularly".

Still referring to FIG. 3, GUI 300 may include toxic element list 308. Toxic element list 312 may display one or more toxic elements of an article of interest. In some embodiments, toxic element list 312 may display one or more toxic elements according to a rank of toxicity. GUI 300 may include symptom list 316. Symptom list 316 may include one or more symptoms associated with one or more toxic elements of an article of interest. In some embodiments, symptom list 316 may include a ranked list according to symptom severity. In some embodiments GUI 300 may display user reviews 320. User reviews 320 may display reviews from other users. In some embodiments, user reviews 320 may display, without limitation, a pop-up window, drop-down list, and the like. In some embodiments, user reviews 320 may be configured to display one or more user reviews, and/or an average ranking thereof. User reviews 320 may include without limitation a toxic load quantifier, description of symptoms, reactions to toxic elements, and the like. In some embodiments, GUI 300 may display alternative products 324. Alternative products 324 may include alternative articles of interest. In some embodiments, alternative products 324 may include articles of interest with higher user reviews, higher toxic load quantifier, lower cost, similar articles of interest, and the like.

Figure 4:
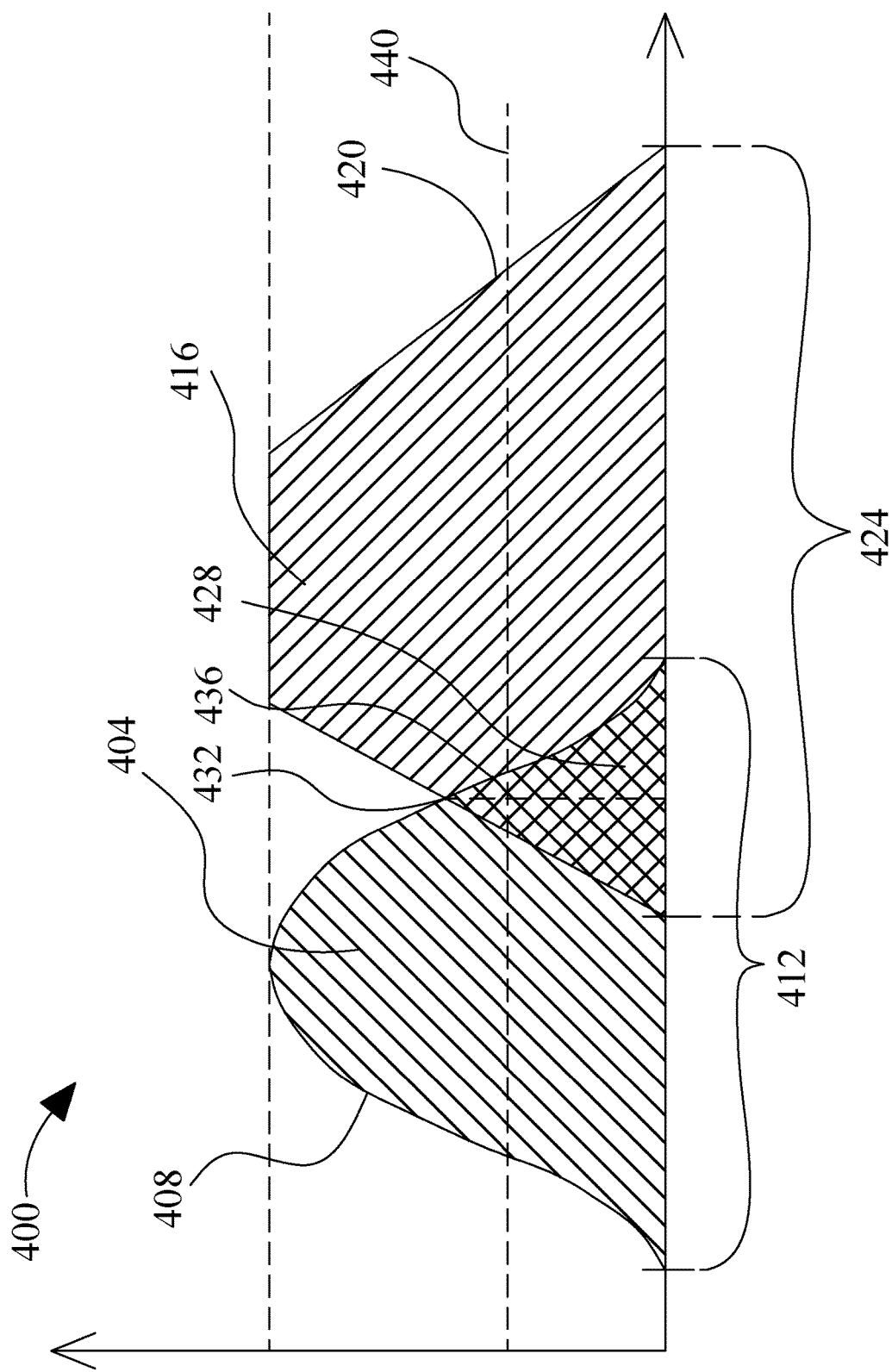
FIG. 4 is an exemplary embodiment of a fuzzy logic system.

Referring to FIG. 4, an exemplary embodiment of fuzzy set comparison 400 is illustrated. A first fuzzy set 404 may be represented, without limitation, according to a first membership function 408 representing a probability that an input falling on a first range of values 412 is a member of the first fuzzy set 404, where the first membership function 408 has values on a range of probabilities such as without limitation the interval [0,1], and an area beneath the first membership function 408 may represent a set of values within first fuzzy set 404. Although first range of values 412 is illustrated for clarity in this exemplary depiction as a range on a single number line or axis, first range of values 412 may be defined on two or more dimensions, representing, for instance, a Cartesian product between a plurality of ranges, curves, axes, spaces, dimensions, or the like. First membership function 408 may include any suitable function mapping first range 412 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 4, first fuzzy set 404 may represent any value or combination of values as described above, including output from one or more machine-learning models and articles of interest, a predetermined class, such as without limitation a toxic load quantifier. A second fuzzy set 416, which may represent any value which may be represented by first fuzzy set 404, may be defined by a second membership function 420 on a second range 424; second range 424 may be identical and/or overlap with first range 412 and/or may be combined with first range via Cartesian product or the like to generate a mapping permitting evaluation overlap of first fuzzy set 404 and second fuzzy set 416. Where first fuzzy set 404 and second fuzzy set 416 have a region 428 that overlaps, first membership function 408 and second membership function 420 may intersect at a point 432 representing a probability, as defined on probability interval, of a match between first fuzzy set 404 and second fuzzy set 416. Alternatively or additionally, a single value of first and/or second fuzzy set may be located at a locus 436 on first range 412 and/or second range 424, where a probability of membership may be taken by evaluation of first membership function 408 and/or second membership function 420 at that range point. A probability at 428 and/or 432 may be compared to a threshold 440 to determine whether a positive match is indicated. Threshold 440 may, in a non-limiting example, represent a degree of match between first fuzzy set 404 and second fuzzy set 416, and/or single values therein with each other or with either set, which is sufficient for purposes of the matching process; for instance, threshold may indicate a sufficient degree of overlap between an output from one or more machine-learning models and/or an article of interest and a predetermined class, such as without limitation a toxic load quantifier for combination to occur as described above. Alternatively or additionally, each threshold may be tuned by a machine-learning and/or statistical process, for instance and without limitation as described in further detail below.

Further referring to FIG. 4, in an embodiment, a degree of match between fuzzy sets may be used to classify an article of interest with a toxic load quantifier. For instance, if an article of interest has a fuzzy set matching a toxic load quantifier fuzzy set by having a degree of overlap exceeding a threshold, apparatus 100 may classify the article of interest as belonging to the toxic load quantifier fuzzy set. Where multiple fuzzy matches are performed, degrees of match for each respective fuzzy set may be computed and aggregated through, for instance, addition, averaging, or the like, to determine an overall degree of match.

Still referring to FIG. 4, in an embodiment, an article of interest may be compared to multiple toxic load quantifier fuzzy sets. For instance, an article of interest may be represented by a fuzzy set that is compared to each of the multiple toxic load quantifier fuzzy sets; and a degree of overlap exceeding a threshold between the article of interest fuzzy set and any of the multiple toxic load quantifier fuzzy sets may cause apparatus 100 to classify the article of interest as belonging to a toxic load quantifier fuzzy set. For instance, in one embodiment there may be two toxic load quantifier fuzzy sets, representing respectively a high toxic load quantifier fuzzy set and a moderate toxic load quantifier fuzzy set. A high toxic load quantifier fuzzy set may have a first fuzzy set; a moderate toxic load quantifier fuzzy set may have a second fuzzy set; and articles of interest may have an articles of interest fuzzy set. Apparatus 100, for example, may compare an article of interest fuzzy set with each of a high toxic load quantifier fuzzy set and a moderate toxic load quantifier fuzzy set, as described above, and classify an article of interest to either, both, or neither of a high toxic load quantifier fuzzy set or a moderate toxic load quantifier fuzzy set. Machine-learning methods as described throughout may, in a non-limiting example, generate coefficients used in fuzzy set equations as described above, such as without limitation x, c, and σ of a Gaussian set as described above, as outputs of machine-learning methods. Likewise, an article of interest may be used indirectly to determine a fuzzy set, as an article of interest fuzzy set may be derived from outputs of one or more machine-learning models that take the article of interest directly or indirectly as inputs.

Still referring to FIG. 4, a computing device may use a logic comparison program, such as, but not limited to, a fuzzy logic model to determine a toxic load quantifier. A toxic load quantifier may include, but is not limited to, low, average, high, and the like; each such toxic load quantifier may be represented as a value for a linguistic variable representing a toxic load quantifier or in other words a fuzzy set as described above that corresponds to a degree of toxic load as calculated using any statistical, machine-learning, or other method that may occur to a person skilled in the art upon reviewing the entirety of this disclosure. In other words, a given element of an article of interest may have a first non-zero value for membership in a first linguistic variable value such as "1" and a second non-zero value for membership in a second linguistic variable value such as "2". In some embodiments, determining a toxic load quantifier may include using a linear regression model. A linear regression model may include a machine learning model. A linear regression model may be configured to map data of an article of interest and/or user data, such as ingredients of an article of interest, to one or more toxic load quantifiers. A linear regression model may be trained using training data correlating articles of interest to toxic load quantifiers. A linear regression model may map statistics such as, but not limited to, toxic load impact magnitude, frequency of articles of interest of toxic load quantifiers, and the like. In some embodiments, determining a toxic load quantifier of an article of interest may include using a toxic load quantifier classification model. A toxic load quantifier classification model may be configured to input collected data and cluster data to a centroid based on, but not limited to, frequency of appearance, linguistic indicators of toxic elements, and the like. Centroids may include scores assigned to them such that elements of articles of interest may each be assigned a score. In some embodiments, a toxic load quantifier classification model may include a K-means clustering model. In some embodiments, a toxic load quantifier classification model may include a particle swarm optimization model. In some embodiments, determining a toxic load quantifier of an article of interest may include using a fuzzy inference engine. A fuzzy inference engine may be configured to map one or more article of interest data elements using fuzzy logic. In some embodiments, a plurality of entity assessment devices may be arranged by a logic comparison program into toxic load quantifier arrangements. A "toxic load quantifier arrangement" as used in this disclosure is any grouping of objects and/or data based on skill level and/or output score. This step may be implemented as described above in FIGS. 1-3 and below in FIG. 5. Membership function coefficients and/or constants as described above may be tuned according to classification and/or clustering algorithms. For instance, and without limitation, a clustering algorithm may determine a Gaussian or other distribution of questions about a centroid corresponding to a given toxic load level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 4, an inference engine may be implemented according to input and/or output membership functions and/or linguistic variables. For instance, a first linguistic variable may represent a first measurable value pertaining to elements of an article of interest such as a degree of toxicity of an element of an article of interest, while a second membership function may indicate a degree of toxic load impact of a subject thereof, or another measurable value pertaining to an article of interest. Continuing the example, an output linguistic variable may represent, without limitation, a score value. An inference engine may combine rules, such as: "if the article of interest has 'high amounts of a toxic element' and the usage frequency is 'high', the toxic load quantifier is 'high'"—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 4, an article of interest to be used may be selected by user selection, and/or by selection of a distribution of output scores, such as 30% low toxic load quantifiers, 40% moderate toxic load quantifiers, and 30% high toxic load quantifiers or the like. Each ranking may be selected using an additional function such as a degree of toxicity as described above.

Figure 5:
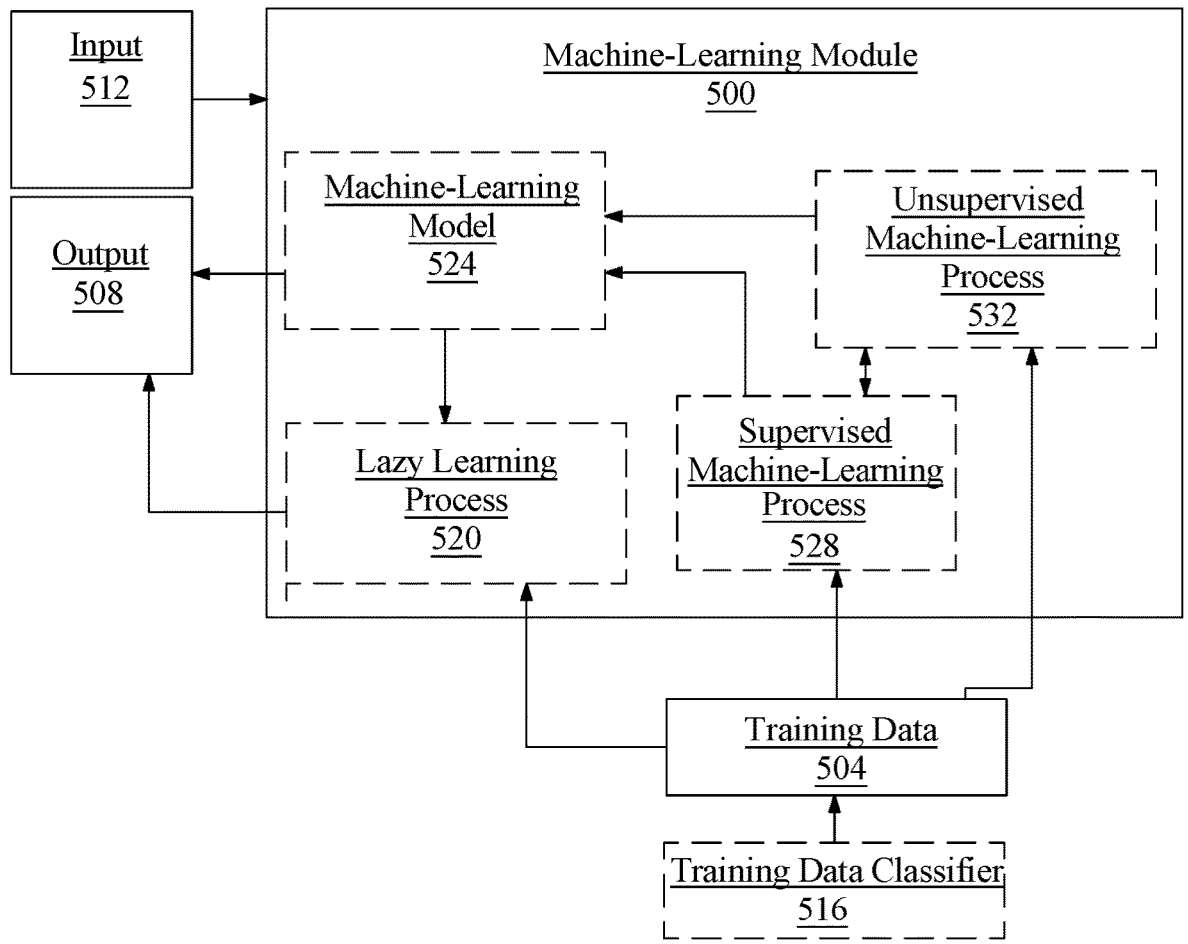
FIG. 5 is an exemplary embodiment of a block diagram of a machine leaning model.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs may include articles of interest and outputs may include toxic load quantifiers.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to categories of articles of interest, toxic load impact levels, toxic element categories, and the like.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include user data as described above as inputs, articles of interest as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
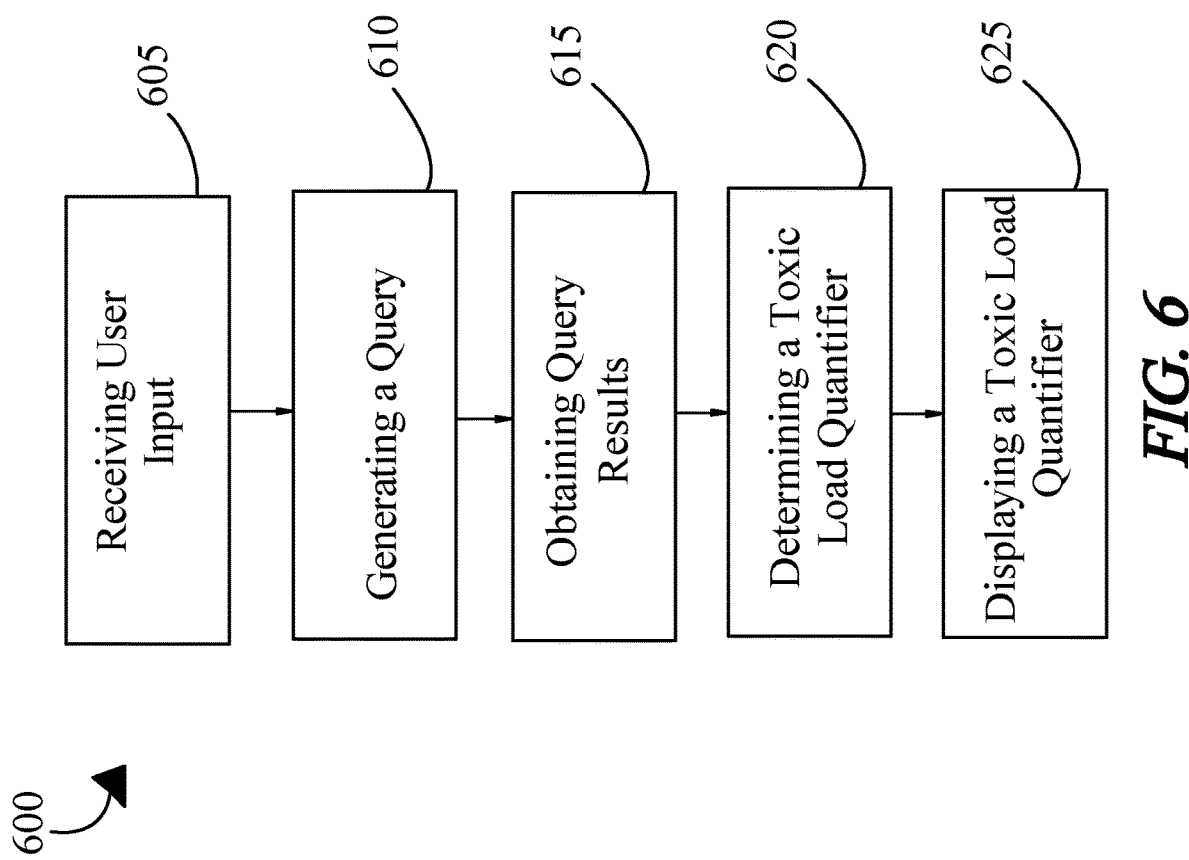
FIG. 6 is an exemplary embodiment of a flow diagram for a method of determining toxic loads.

Referring now to FIG. 6, a method 600 of determining a toxic load quantifier is presented. At step 605, method 600 includes receiving user input. User input may be received through a computing device. User input may comprise first user data. In some embodiments, user input may include, but is not limited to, text entries, selection of computer icons, biological extractions, and the like. This step may be implemented without limitation as described above in FIGS. 1-4.

Still referring to FIG. 6, at step 610, method 600 includes generating a query. A query may be generated to search for one or more articles of interest. In some embodiments, a query may be generated as a function of first user data. This step may be implemented without limitation as described above in FIGS. 1-4.

Still referring to FIG. 6, at step 615, method 600 includes obtaining query results. Query results may include one or more articles of interest. This step may be implemented without limitation as described above in FIGS. 1-4.

Still referring to FIG. 6, at step 620, method 600 includes determining a toxic load quantifier. A toxic load quantifier may be determined as a function of a toxic criterion and/or user data. In some embodiments, a toxic load quantifier may be determined as a function of a machine learning model, classifier, fuzzy logic system, and/or any process described throughout this disclosure. This step may be implemented without limitation as described above in FIGS. 1-4.

Still referring to FIG. 6, at step 625, method 600 displaying a toxic load quantifier. A toxic load quantifier may be displayed through a computing device, such as, but not limited to, a smartphone, web interface, graphical user interface (GUI), and the like. In some embodiments, a toxic load quantifier may be displayed in an ascending and/or descending order according to a criterion. This step may be implemented without limitation as described above in FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
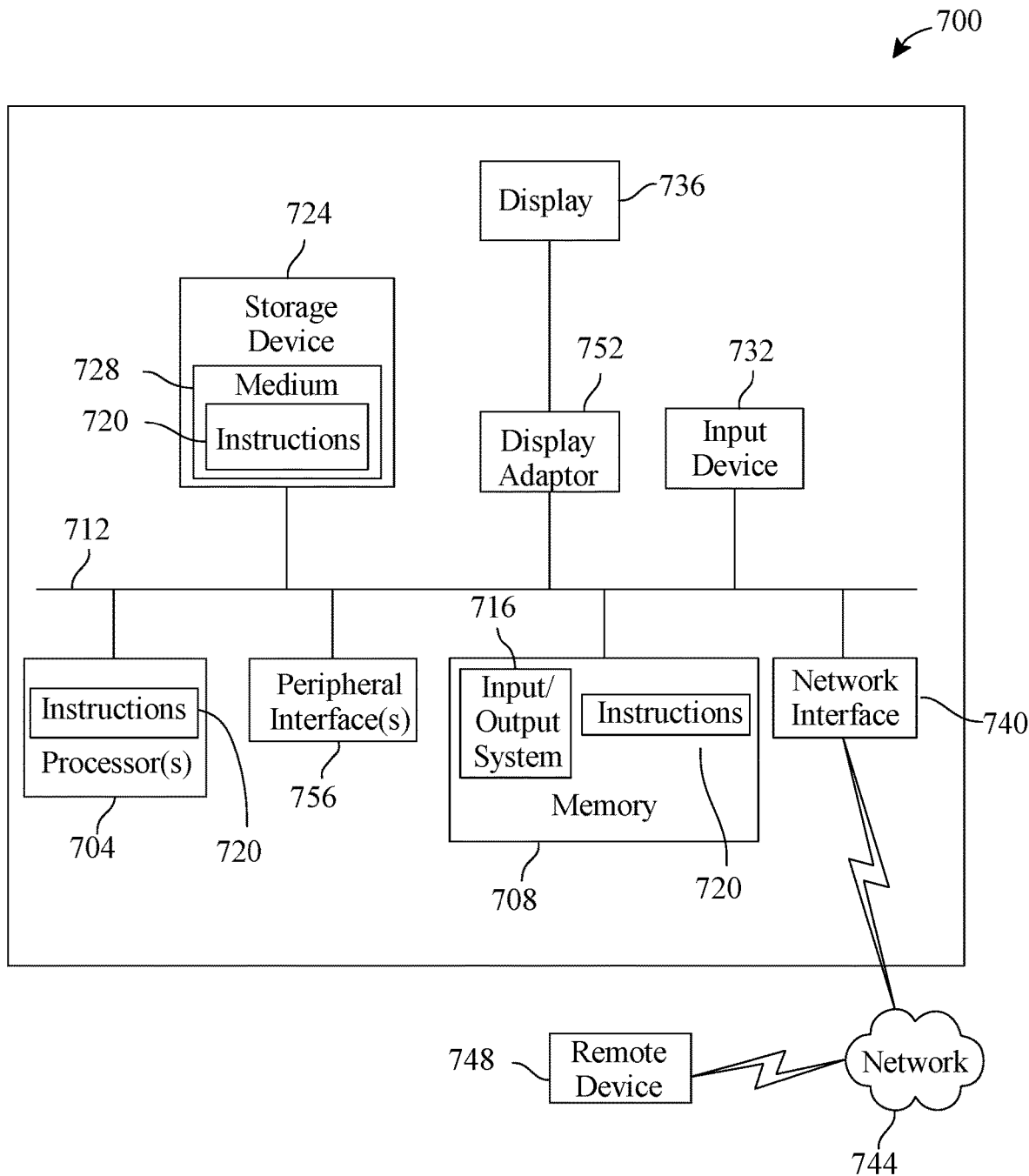
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for determining toxic load quantifiers, comprising:
   at least a processor and a memory communicatively connected to the at least a processor, the memory containing instructions configuring the at least a processor to:
   receive user input comprising first user data obtained from a physically extracted sample of the user, wherein the physically extracted sample of the user indicates an absorption ability of the user;
   determine a toxin profile, wherein determining the toxin profile comprises:
   receiving first training data correlating environmental elements to toxic element exposure levels;
   training an environmental exposure classifier using the first training data and a first machine learning algorithm, wherein the environmental exposure classifier is configured to input first user data obtained from the physically extracted sample of the user and output toxin profiles; and
   determining as a function of the first user data and the environmental exposure classifier, the toxin profile;
   generate a query as a function of the first user data, wherein the query comprises an article of interest;
   obtain at least a query result as a function of the query, wherein obtaining the at least query result comprises:
   generating an objective function; and
   optimizing the objective function as a function of the article of interest;
   determine, as a function of a toxicity criterion and the first user data, a toxic load quantifier of the at least a query result, wherein the toxic load quantifier is based on an absorption rate of toxic elements in the article of interest indicated by the physically extracted sample of the user, wherein determining the toxic load quantifier comprises:
   receiving second training data correlating query results to toxic load rankings;

training a toxic load machine learning model using the second training data and a second machine learning algorithm, wherein the toxic load machine learning model is configured to input query results and output toxic load rankings; and determining, as a function of the obtained query result and the toxic load machine learning model, a toxic load ranking; and display the toxic load quantifier to a user.

2. The apparatus of claim 1, wherein a toxic element of the toxic load quantifier includes carcinogens.

3. The apparatus of claim 1, wherein a toxic element of the toxic load quantifier includes toxins that affect a user's immune system.

4. The apparatus of claim 1, wherein a toxic element of the toxic load quantifier includes toxins that affect DNA of a user.

5. The apparatus of claim 1, wherein the at least a processor is further configured to generate a cumulative toxin exposure model.

6. The apparatus of claim 1, wherein the at least a processor is further configured to determine the toxic load quantifier specific to a user.

7. The apparatus of claim 1, wherein the at least a processor is further configured to generate a detoxing protocol.

8. The apparatus of claim 7, wherein the at least a processor is configured to:
receive second user data; and
adjust the detoxing protocol as a function of the second user data.

9. The apparatus of claim 1, wherein the at least a processor is further configured to generate a prophylaxis protocol as a function of the toxic load quantifier.

10. The apparatus of claim 1, wherein the at least a processor is further configured to classify environmental exposures to toxic element exposure levels using the environmental exposure classifier.

11. The apparatus of claim 1, wherein the first user data includes an article of interest, and the at least a processor is further configured to display alternative articles of interest as a function of the toxic load quantifier.

12. The apparatus of claim 1, wherein the first user data further includes an article of interest, and the at least a processor is further configured to determine a toxic load impact of the article of interest.

13. The apparatus of claim 1, wherein the at least a processor is further configured to generate the toxin profile as a function of the user input and the toxic load quantifier.

14. A method of using a computing device for determining toxic load quantifiers, comprising:

receiving user input comprising first user data obtained from a physically extracted sample of the user, wherein the physically extracted sample of the user indicates an absorption ability of the user;

determining a toxin profile, wherein determining the toxin profile comprises:
receiving first training data correlating environmental elements to toxic element exposure levels;
training an environmental exposure classifier using the first training data and a first machine learning algorithm, wherein the environmental exposure classifier is configured to input first user data obtained from the physically extracted sample of the user and output toxin profiles; and
determining as a function of the first user data and the environmental exposure classifier, the toxin profile;

generating a query as a function of the first user data, wherein the query comprises an article of interest;

obtaining at least a query result as a function of the query, wherein obtaining the at least query result further comprises:
generating an objective function; and
optimizing the objective function as a function of the article of interest;

determining, as a function of a toxicity criterion and the first user data, a toxic load quantifier of the at least a query result, wherein the toxic load quantifier is based on an absorption rate of toxic elements in the article of interest indicated by the physically extracted sample of the user; wherein determining the toxic load quantifier comprises:
receiving second training data correlating query results to toxic load rankings;
training a toxic load machine learning model using the second training data and a second machine learning algorithm, wherein the toxic load machine learning model is configured to input query results and output toxic load rankings; and
determining, as a function of the obtained query result and the toxic load machine learning model, a toxic load ranking; and displaying the toxic load quantifier to a user.

15. The method of claim 14, wherein displaying further comprises displaying alternative articles of interest to the user as a function of the toxic load quantifier of the query results.

16. The method of claim 14, wherein determining further comprises determining a toxic load impact of the article of interest of the at least a query result.

* * * * *